United States Patent [19]
Burkett et al.

[11] Patent Number: 5,728,146
[45] Date of Patent: Mar. 17, 1998

[54] THERMAL NECK WRAP HAVING WING SHAPE AND MEANS FOR POSITION MAINTENANCE

[75] Inventors: Timothy A. Burkett, West Chester; Kurt E. Holstein, Cincinnati; Elizabeth M. Harvey, West Chester; William R. Ouellette, Cincinnati, all of Ohio

[73] Assignee: The Procter & Gamble Company, Cincinnati, Ohio

[21] Appl. No.: 746,359

[22] Filed: Nov. 8, 1996

Related U.S. Application Data

[63] Continuation of Ser. No. 496,716, Jun. 29, 1995, abandoned.

[51] Int. Cl.$^6$ .......................................................... A61F 7/00
[52] U.S. Cl. .............................. 607/109; 607/114; 165/46
[58] Field of Search ..................... 607/96, 104, 108–112, 607/114; 126/204; 165/46

[56] References Cited

U.S. PATENT DOCUMENTS

| | | |
|---|---|---|
| 3,149,943 | 9/1964 | Amador . |
| 3,667,462 | 6/1972 | Moor . |
| 3,736,769 | 6/1973 | Peterson . |
| 3,882,867 | 5/1975 | Moran . |
| 3,893,460 | 7/1975 | Karami . |
| 3,900,035 | 8/1975 | Welch et al. . |
| 3,955,575 | 5/1976 | Okuda . |
| 3,976,049 | 8/1976 | Yamashita et al. . |
| 4,044,773 | 8/1977 | Baldwin, III . |
| 4,081,150 | 3/1978 | Tyson . |
| 4,190,054 | 2/1980 | Brennan . |
| 4,204,543 | 5/1980 | Henderson . |
| 4,243,041 | 1/1981 | Paul . |
| 4,255,157 | 3/1981 | Yamaguchi et al. . |
| 4,268,272 | 5/1981 | Taura . |
| 4,282,005 | 8/1981 | Sato et al. . |
| 4,366,804 | 1/1983 | Abe . |
| 4,516,564 | 5/1985 | Koiso et al. . |
| 4,527,566 | 7/1985 | Abare . |
| 4,575,097 | 3/1986 | Brannigan et al. . |
| 4,586,506 | 5/1986 | Nangle . |
| 4,628,918 | 12/1986 | Johnson, Jr. . |
| 4,628,932 | 12/1986 | Tampa . |

(List continued on next page.)

FOREIGN PATENT DOCUMENTS

| | | |
|---|---|---|
| 0 014 300 A1 | 8/1980 | European Pat. Off. . |
| 0 324 578 A1 | 7/1989 | European Pat. Off. . |
| 0 370 600 A1 | 5/1990 | European Pat. Off. . |
| 2 687 912 A1 | 3/1993 | France . |
| 160433 | 7/1987 | India . |
| 58-132074 | 8/1983 | Japan . |
| 6-241575 | 8/1994 | Japan . |
| 7-124192 | 5/1995 | Japan . |
| 7-194642 | 8/1995 | Japan . |
| 2 205 496 | 1/1988 | United Kingdom . |
| WO 94/00087 | 6/1994 | WIPO . |
| WO 94/12125 | 9/1994 | WIPO . |

*Primary Examiner*—Jennifer Bahr
*Assistant Examiner*—Ryan Carter
*Attorney, Agent, or Firm*—Ronald W. Kock

[57] ABSTRACT

A substantially triangular piece of flexible material, which has the appearance of a delta-winged aircraft when flattened. The piece of flexible material has a first wing portion, a second wing portion, a central body portion therebetween, and a body-facing side. The neck wrap also has a plurality of individual thermal elements embedded therein. The plurality of thermal elements have a pattern which approximates the shape and location of muscles in the user's upper back, lower neck, and shoulders. The pattern has a gap bisecting the central portion corresponding to the user's spine. The neck wrap maintains piece of flexible material in a desired position once the piece of flexible material has been draped over the user's shoulders. The central portion is centered at the user's upper back and lower neck and the first and second wing portions lay across the user's shoulders and rest on the user's chest. The device for maintaining the piece of flexible material in position includes counterweights attached to the first and second wing portions in order to balance the thermal elements in the central portion and at least one strip of foamed polymer attached to each of the first and second wing portions on said body-facing side thereof.

11 Claims, 2 Drawing Sheets

U.S. PATENT DOCUMENTS

| | | |
|---|---|---|
| 4,669,476 | 6/1987 | Gordon et al. |
| 4,671,267 | 6/1987 | Stout |
| 4,706,658 | 11/1987 | Cronin |
| 4,756,299 | 7/1988 | Podella |
| 4,802,667 | 2/1989 | Altner |
| 4,805,620 | 2/1989 | Meistrell |
| 4,860,748 | 8/1989 | Chiurco et al. |
| 4,886,063 | 12/1989 | Crews |
| 4,891,501 | 1/1990 | Lipton |
| 4,914,717 | 4/1990 | Gibbon |
| 4,925,743 | 5/1990 | Ikeda et al. |
| 4,961,418 | 10/1990 | McLaurin-Smith |
| 4,972,832 | 11/1990 | Trapini et al. |
| 4,981,135 | 1/1991 | Hardy |
| 5,000,176 | 3/1991 | Daniel |
| 5,007,416 | 4/1991 | Burns et al. |
| 5,027,801 | 7/1991 | Grim |
| 5,046,479 | 9/1991 | Usui |
| 5,062,269 | 11/1991 | Siegel |
| 5,065,758 | 11/1991 | Whitehead et al. |
| 5,072,598 | 12/1991 | Dibrell |
| 5,086,629 | 2/1992 | Dibrell |
| 5,086,761 | 2/1992 | Ingram |
| 5,088,487 | 2/1992 | Turner |
| 5,088,549 | 2/1992 | Schneider |
| 5,094,238 | 3/1992 | Gibbon |
| 5,133,348 | 7/1992 | Mayn |
| 5,165,402 | 11/1992 | McCoy |
| 5,179,944 | 1/1993 | McSymytz |
| 5,190,033 | 3/1993 | Johnson |
| 5,211,623 | 5/1993 | Sarkozi |
| 5,233,981 | 8/1993 | Miyashita |
| 5,269,023 | 12/1993 | Ross |
| 5,342,412 | 8/1994 | Ueki |
| 5,366,491 | 11/1994 | Ingram et al. |
| 5,373,582 | 12/1994 | Dragone et al. |
| 5,375,261 | 12/1994 | Lipke |
| 5,378,225 | 1/1995 | Chatman, Jr. |
| 5,398,667 | 3/1995 | Witt |
| 5,399,130 | 3/1995 | Saunders |
| 5,451,201 | 9/1995 | Prengler |
| 5,496,357 | 3/1996 | Jensen et al. |
| 5,500,959 | 3/1996 | Yewer, Jr. |
| 5,534,021 | 7/1996 | Dvoretzkky et al. |

THERMAL NECK WRAP HAVING WING SHAPE AND MEANS FOR POSITION MAINTENANCE

This is a continuation of appl. Ser. No. 08/496,716, filed on Jun. 29, 1995 now abandoned.

FIELD OF THE INVENTION

The present invention relates to neck wraps having thermal sources for temporary pain relief application, and more particularly to neck wraps wherein thermal energy is applied to specific areas of the upper back, neck and shoulders. Even more particularly, the present invention relates to neck wraps having position maintenance features.

BACKGROUND OF THE INVENTION

Upper back, neck, and shoulder pain is associated with stress, bursitis, and upper back and neck muscular problems. Heating pads and ice packs are common devices used to relieve such pain. However, these pain relieving devices are typically inconvenient to use on a regular and extended basis because: thermal energy may not be immediately available when needed; thermal energy may not be released in a controllable or sustainable manner; and/or proper positioning of thermal energy elements may not be maintainable during body movement.

What is needed is an inexpensive disposable neck wrap which can be worn under outer clothing with minimal visibility, which provides instant heating or cooling in a controlled and sustainable manner, which has alignment and position maintenance features, and which has a thermal element pattern that directs thermal energy to where it has the most temporary pain relief benefit.

SUMMARY OF THE INVENTION

In one aspect of the present invention a thermal neck wrap comprises a substantially triangular piece of flexible material, which has the appearance of a swept-winged aircraft when flattened. The piece of flexible material has a first wing portion, a second wing portion, a central body portion therebetween, and a body-facing side. The neck wrap also has a plurality of individual thermal elements embedded in the piece of flexible material. The plurality of thermal elements have a pattern which approximates the shape and location of muscles in the user's upper back, lower neck, and shoulders. The pattern has a gap bisecting the central portion corresponding to the user's spine. The neck wrap also has means for maintaining the piece of flexible material in a desired position once the piece of flexible material has been draped over the user's shoulders. The central portion is centered at the user's upper back and lower neck and the first and second wing portions lay across the user's shoulders and rest on the user's chest.

The means for maintaining the piece of flexible material in position comprises counterweights attached to the first and second wing portions in order to balance the thermal elements in the central portion. The counterweights in both wing portions total from 40 to 80 grams of weight. The means for maintaining the thermal neck wrap in position may also comprise at least one strip of foamed polymer attached to each of the first and second wing portions on the body-facing side thereof. The strip of foamed polymer reduces slip between the piece of flexible material and the user's body and inner clothing. The strip of foamed polymer also serves as a visual aid in applying the thermal neck wrap and identifying the body-facing side so that oxygen may permeate from the thermal elements through a wrap side opposite the body-facing side.

The plurality of thermal elements in the neck wrap are individually spaced apart and connected to the piece of flexible material so that the piece of flexible material may fold, buckle, and bend between the thermal elements to accommodate the user's arm and shoulder movements without misaligning the thermal neck wrap relative to the user's upper back, neck, and shoulder muscles.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1A:
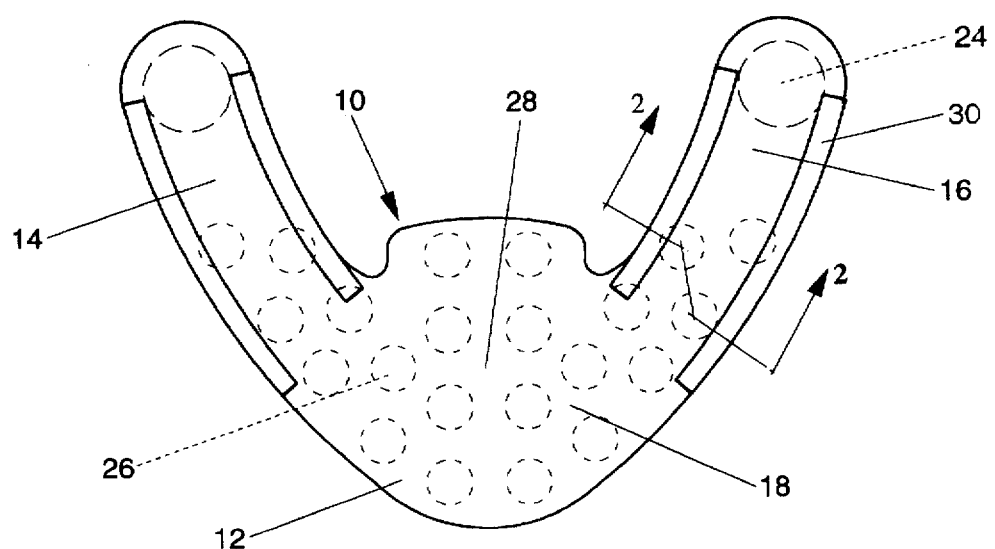
FIG. 1A is a top plan view of a preferred embodiment of the neck wrap of the present invention, showing the preferred wing shape and pattern of heating units.
Figure 2:
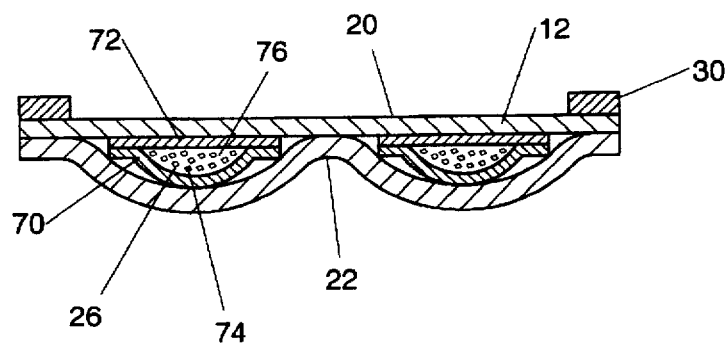
FIG. 2 is a sectioned elevation view of the embodiment of FIG. 1A, taken along section line 2—2 of FIG. 1A, showing individual thermal cells embedded within the neck wrap.
Figure 1B:
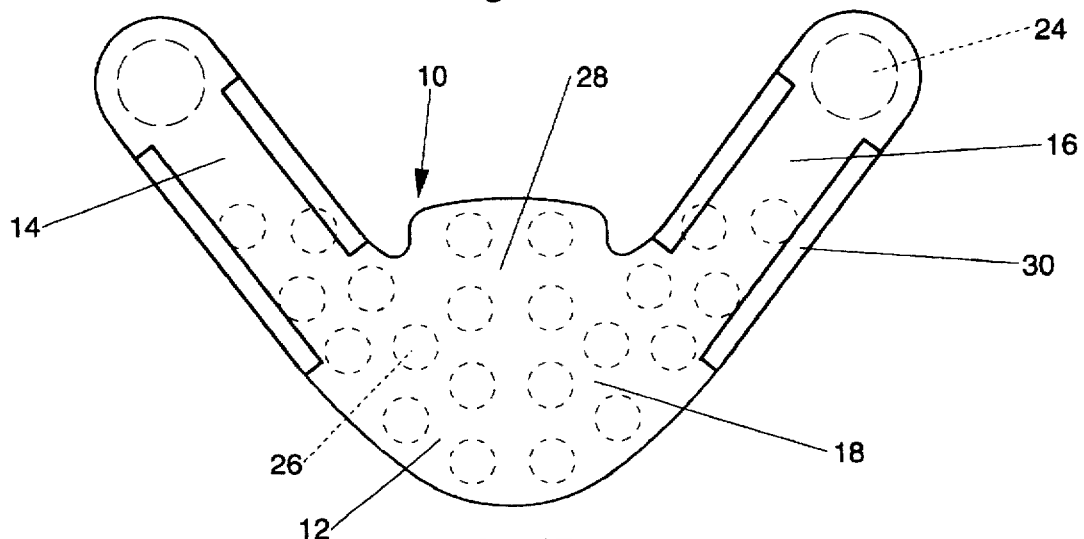
FIG. 1B is a top plan view of an alternative embodiment of the neck wrap of the present invention, showing an alternative wing shape and pattern of heating units.
Figure 3:
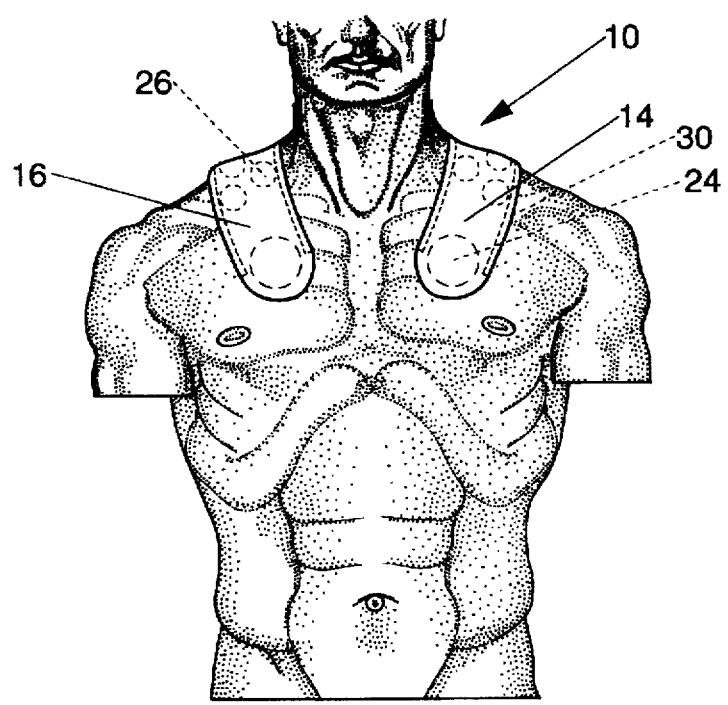
FIG. 3 is a perspective view thereof, showing the neck wrap draped over a user's shoulders, positioned by counterweights and high friction surfaces.
Figure 4:
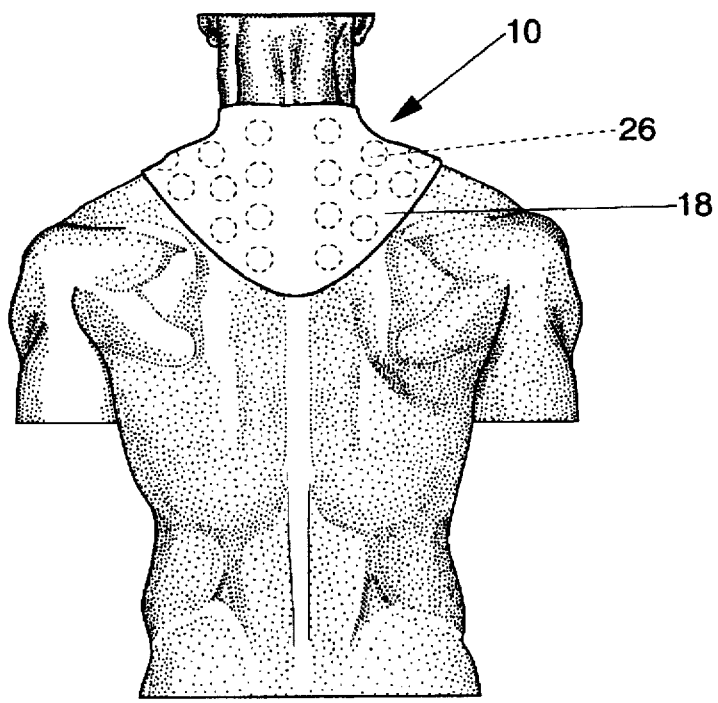
FIG. 4 is a perspective view thereof, showing the location of the neck wrap and its thermal pattern relative to the muscles of the neck and upper back.

Referring now to the drawings, and more particularly to FIGS. 1A and 2, there is shown a preferred embodiment of the present invention which provides a thermal neck wrap with wing shape and means for position maintenance, which is generally indicated as 10. Thermal neck wrap 10 is made from a substantially triangular piece of flexible material 12 which, when it is planar or flattened, has the appearance of a swept-wing aircraft. Wrap 10 has a first wing portion 14, a second wing portion 16, and a central body portion 18 therebetween. Wing portions 14 and 16 may have either curved edges as depicted in FIG. 1A or straight edges as depicted in FIG. 1B. Wrap 10 has a body facing side 20 and an opposing outer side 22. When neck wrap 10 is worn, wing portions 14 and 16 extend over the shoulders of the wearer onto the upper chest, as depicted in FIG. 3. Central body portion 18 is located on the upper back and neck of the wearer, as depicted in FIG. 4.

Thermal neck wrap 10 has a plurality of individual thermal elements 26 embedded therein. Thermal elements 26 are positioned within central body portion 18 and wings 14 and 16. When wrap 10 is properly positioned on the user, thermal elements 26 approximate the shape and location of muscles in the user's upper back, lower neck and shoulders. Within the pattern of thermal elements 26 there is a gap 28 bisecting central body portion 18. Gap 28 contains no thermal elements 26. Gap 28 corresponds to the spinal area of the user and is located so as to minimize the application of direct thermal energy to the spine of the user.

Thermal elements 26 may be either enclosed entirely within flexible material 12 as depicted in FIG. 2 or alternatively thermal elements 26 may be attached to either body-facing side 20 or opposing outer side 22. Thermal elements 26 are preferably spaced apart from one another and connected to flexible material 12 as depicted in FIG. 2.

During use, thermal neck wrap 10 is draped over the shoulders of the wearer. Preferably, first and second wing portions 14 and 16 have weights 24 placed in their distal ends. Weights 24 are located on the upper chest of the wearer as depicted in FIG. 3 and serve to counterbalance the weight of thermal elements 26 which are located substantially on the back of the wear during use. In a preferred embodiment of the present invention, weights 24 are about twenty to forty grams each, for a total counterbalancing weight of forty to eighty grams within wrap 10.

Thermal neck wrap 10 preferably has at least one foamed polymer strip 30 attached to each of first wing portion 14 and second wing portion 16 on body-facing side 20. Foamed polymer strips 30 provide increased friction between wrap 10 and the wearer in order to reducing slipping or relative movement between wrap 10 and the wearer during use. Preferably, foamed polymer strips 30 may have a color different from that of material 12. This color difference could function as a visual aid by helping the wearer to identify body-facing side 20 of wrap 10 for proper application.

Flexible material 12 of wrap 10 may be selected from any number of suitable materials including but not limited to: wovens, knits, films, foams and nonwovens, including spunbond, carded, meltblown, hydroentangled, through-air bonded, air laid, and wet laid. These materials may be made from natural fibers including but limited to: cotton; wool; linen; or manmade polymeric materials such as: polypropylene, polyester, nylon, polyethylene, metallocene catalyst polyethylene, etc.

A particularly preferred embodiment of the present invention is made using the following materials and method. A film of Styrene Block Copolymer (SBC) is combined with two layers of polypropylene (PP) spunbond nonwoven. A trilaminate is made by stretching the elastic SBC about 100% (twice its original length). While the SBC is held in this strained position, a layer of PP nonwoven is positioned on each side of the SBC and ultrasonically bonded together to in a discrete pattern. The trilaminate is then released and allowed to return to a relaxed position. The PP nonwoven is gathered or puckered between the discrete bonding sites. An SBC that has been successfully used is a 0.0024 inch (2.4 mil) thick EXX500D which is produced by Exxon Chemicals of Lake Zurich, Ill. Nonwovens that have been successfully used are a 14 gram/square yard (gsy) and a 17 gsy spunbond PP available from Veratec, Walpole, Mass. The combining operation (stretching, combining, bonding) has been done by Veratec, Walpole, Mass. The resulting trilaminate elastic material is available from Veratec as PO671.0. This trilaminate is then laminated to a second web material which is a carded/hydroentangled polyester nonwoven. The second lamination is achieved using a pressure sensitive hot melt glue available from Findley Adhesives, Wawautosa, Wis., as #2031. The glue is applied via a spiral pattern by Waytek of Springboro, Ohio, at a level of about 0.002 to 0.006 grams per square inch. The polyester nonwoven is available from Veratec, Walpole, Mass., as #140060 PET.

Weights that have been successfully used are 2.13 inch diameter 16 gauge galvanized steel slugs made by Cincinnati Ventilation of Florence, Ky. Any number of suitable materials could be used to provide the counterweight needed. Weights are preferably placed about 12 mm from the ends of first and second wing portions and are held in place by the same pressure sensitive hot melt adhesive #2031 noted herebefore.

Foamed polymer strips are used to provide additional friction between the wrap and the wearer. The foamed polymer used is a Polyurethene foam available from General Foam of East Rutherford, N.J., as 40330303 blue foam. This foam is available in a number of colors including white and pink. The foamed polymer strips are attached to the wrap using the same pressure sensitive hot melt glue #2031 noted herebefore. The glue is applied in a spiral pattern by Waytek of Springboro, Ohio, at a level of about 0.002 to 0.006 grams per square inch.

The trilaminate is used to provide bulk via the rugosities of the gathered spunbond webs, while maintaining the drape of a fabric. Other suitable material that could be utilized would include but not be limited to: through-air bonded nonwovens; needled, felted, or hydroentangled nonwovens; wovens or knits; or multiple layers of the aforementioned webs. The hydroentangled polyester which is used in the present invention as the second layer serves as the body contacting side of the product. The purpose of this material is to provide a soft, conforming, skin friendly surface for the wearer. Other suitable materials would be nonwovens, which are spunbonded, carded, airlaid, thermal bonded, through-air bonded, hydroentangled, or wovens, or knits. These materials could be made of natural fibers, such as cotton or linen, or synthetic fibers, such as polypropylene, polyester, polyethylene, nylon, rayon, etc.

The materials from which the wrap are constructed must be selected such that once they are combined in the product the product must be adapted to both easily drape over and conform to the body curvature and to provide minimal translation of compressive force along and in the plane of the product. In the present invention the trilaminate, in a relaxed or zero-strain condition, and the polyester web, are combined with a pressure sensitive hot melt glue. This glue is applied via a spiral glue application system at a level of approximately 0.002 to 0.006 grams per square inch. Other suitable combining or assembly means can include but not be limited to: thermal dot bonding, melt blown hot melt glue, bead applied hot melt glue, ultrasonic, or pressure bonding.

It is necessary for the product to easily drape and conform to the body of the wearer to ensure intimate contact with the wearer during use. This intimate contact ensures that thermal energy is delivered properly and that frictional forces between the wearer and the product are maintained to minimize relative movement. The proper drape required is like that of a fabric as opposed to that of a paper. When a fabric is supported by a point force the fabric "breaks" or folds along multiple lines whereas a paper supported by the same point force will normally fold along a single line. Since the thermal neck wrap should conform to the body in an area containing multiple compound curves, this "fabric-like" behavior is helpful.

It is also helpful for the thermal neck wrap to provide minimal translation of any compressive forces within the plane(s) of the product. This means that if one side or edge of the product is subjected to a minimal compressive (or pushing) force that the product will buckle or fold locally and not transmit the force to other parts of the wrap. An example of this effect would be if wearer of the product lifted one arm (i.e. the right). In so doing the upper right shoulder is rotated inward toward the neck. This inward movement of the shoulder produces a force on the right edge of the wrap. Preferably, the wrap buckles or folds on the right side only and therefore maintains its overall positioning relative to the user's body.

Thermal elements 26 are preferably heating elements, which are described in a copending application Ser. No. 08/496,639 entitled "A HEAT CELL", filed on the same day as the present application, and obligated to be assigned to the assignee of the present application, which is hereby incorporated by reference. A preferred heat cell comprises from about 30% to about 80% iron powder; from about 3% to about 25% activated carbon, non-activated carbon, and mixtures thereof; from about 0.5% to about 10% metal salt; and from about 1% to about 40% water; wherein the particles of the particulate exothermic composition are combined in a cell, formed in a unified structure comprising at least two opposed surfaces, wherein at least one surface is oxygen permeable, that when filled with said particulate exothermic composition, has a fill volume and a cell volume whereby the ratio of fill volume to cell volume is from about 0.7 to about 1.0, wherein the ratio is maintained without the use of differential pressure across the cell wall. All percentages and ratios used herein are by weight of the total composition, and all measurements are made at 25° C., unless otherwise specified. Thermal elements 26 are constructed by thermoforming base material 70 to form a pocket 76. Pocket 76 in base material 70 is then filled with chemistry 74. After filling pocket 76 in base material 70 with chemistry 74, cover material 72 is placed over pocket 76 and heat sealed to base material 70 around the periphery of pocket 76, encapsulating chemistry 74. Small holes are then pierced in base material 70 and/or cover material 72 to allow oxygen to reach chemistry 74.

Base material 70 and cover material 72 may be made of any number of materials capable of containing chemistry 74 and limiting oxygen flow into pocket 76. Materials that have been used successfully are 42 gram per square meter polypropylene spunbond nonwoven which have been extrusion coated with low density polyethylene and/or ethyl vinyl acetate (EVA) at a thickness of 50 to 75 microns. Thermal elements 26 are preferable about 25 mm in diameter and about 6 mm in height. Spinal gap 28 is about 20 mm wide and preferably contains no thermal elements 26.

Chemistry 74 is preferably a mixture of powdered iron, powdered activated charcoal, vermiculite, water, and salt. Mixtures of this type react when exposed to oxygen providing heat for several hours. Prior to use, wrap 10 with thermal elements 26 is enclosed within an oxygen impermeable package. To use wrap 10, the wrap is removed from the oxygen impermeable package allowing oxygen to enter pockets 76 and react with chemistry 74 of thermal elements 26.

Thermal neck wrap 10 has overall dimensions of about 300 mm by about 425 mm. Four anti-slip foam strips 30 are preferably about 12 mm wide, about 150 to 190 mm long, and about 1.5 mm thick. Anti-slip foam strips 30 are preferably placed adjacent the leading and trailing edges of wing portions 14 and 16 on body-side facing side 20 of wrap 10.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A thermal neck wrap comprising:
 a) a substantially triangular piece of flexible material, said piece of flexible material having a first wing portion, a second wing portion, a central body portion therebetween, such that when said neck wrap is placed on a user, said central body portion is centered at a user's upper back and lower neck and said first and second wing portions lay across a user's shoulders;
 b) a plurality of individual thermal elements embedded in and fixedly attached to said central body portion, said plurality of thermal elements having a pattern which approximates a shape and location of muscles in a user's upper back, lower neck, and shoulders, said plurality of thermal elements having an oxygen activated, heat generating chemistry; and
 c) counterweights attached to said first and second wing portions laying across a user's shoulders in order to balance said thermal elements in said central portion at a user's lower neck and upper back so that said thermal neck wrap maintains positioning across a user's shoulders without requiring thermal wrap attachment, said counterweights providing no thermal function.

2. The thermal neck wrap of claim 1 wherein said heat generating chemistry contains a mixture of powdered iron, powdered activated charcoal, water and salt.

3. The thermal neck wrap of claim 1 further comprising at least one strip of foamed polymer attached to each of said first and second wing portions on a body-facing side thereof, said at least one strip of foamed polymer reducing slip between said piece of flexible material and a user's body, so that said thermal neck wrap maintains positioning across a user's shoulders without requiring thermal wrap attachment, said at least one strip of foamed polymer providing no thermal function.

4. The thermal neck wrap of claim 1 wherein said plurality of thermal elements are individually spaced apart and connected to said piece of flexible material so that said piece of flexible material may fold, buckle, and bend between said thermal elements to accommodate a user's arm and shoulder movements without misaligning said thermal neck wrap relative to a user's upper back, lower neck, and shoulders.

5. A thermal neck wrap comprising:
 a) a substantially triangular piece of flexible material, said piece of flexible material having a first wing portion, a second wing portion, a central body portion therebetween, such that when said neck wrap is placed on a user, said central body portion is centered at a user's upper back and lower neck and said first and second wing portions lay across a user's shoulders;
 b) a plurality of individual thermal elements embedded in and fixedly attached to said central body portion, said plurality of thermal elements having a pattern which approximates a shape and location of muscles in a user's upper back, lower neck, and shoulders, said plurality of thermal elements having an oxygen activated, heat generating chemistry; and
 c) at least one strip of foamed polymer attached to each of said first and second wing portions on a body-facing side thereof, said at least one strip of foamed polymer reducing slip between said piece of flexible material and a user's body, so that said thermal neck wrap maintains positioning across a user's shoulders without requiring thermal wrap attachment, said at least one strip of foamed polymer providing no thermal function.

6. The thermal neck wrap of claim 5 wherein said heat generating chemistry contains a mixture of powdered iron, powdered activated charcoal, water and salt.

7. The thermal neck wrap of claim 5 wherein said plurality of thermal elements are individually spaced apart and connected to said piece of flexible material so that said piece of flexible material may fold, buckle, and bend between said thermal elements to accommodate a user's arm and shoulder movements without misaligning said thermal neck wrap relative to a user's upper back, lower neck, and shoulders.

8. A Thermal neck wrap comprising:
   a) a substantially triangular piece of flexible material having a first wing portion, a second wind portion, a central body portion therebetween, such that when said neck wrap is placed on a user, said central body portion is centered at a user's upper back and lower neck and said first and second wing portions lay across a user's shoulders;
   b) a plurality of individual thermal elements embedded in and fixedly attached to said central body portion, said plurality of thermal elements having a pattern which approximates a shape and location of muscles in a user's upper back, lower neck, and shoulders, said plurality of thermal elements having an oxygen activated, heat, generating chemistry, said plurality of thermal elements being individually spaced apart and connected to said piece of flexible material so that said piece of flexible material may fold, buckle, and bend between said thermal elements to accommodate a user's arm and shoulder movements without misaligning said thermal neck wrap relative to a user's upper back, neck and shoulder muscles; and
   c) a means for maintaining said piece of flexible material in a desired position once said piece of flexible material has been laid over a user's shoulders, said pattern having a gap bisecting said central portion, said gap corresponding to a user's spine.

9. The thermal neck wrap of claim 8 wherein said means for maintaining said piece of flexible material in position comprises counterweights attached to said first and second wing portions laying across a user's shoulders in order to balance said thermal elements in said central portion at a user's lower neck and upper back so that said thermal neck wrap maintains positioning across a user's shoulders without requiring thermal wrap attachment, said counterweights providing no thermal function.

10. The thermal neck wrap of claim 8 wherein said means for maintaining said thermal neck wrap in position comprises at least one strip of foamed polymer attached to each of said first and second wing portions on a body-facing side thereof, said at least one strip of foamed polymer reducing slip between said piece of flexible material and a user's body, so that said thermal neck wrap maintains positioning across a user's shoulders without requiring thermal wrap attachment, said at least one strip of foamed polymer providing no thermal function.

11. The thermal neck wrap of claim 8 wherein said heat generating chemistry contains a mixture of powdered iron, powdered activated charcoal, water and salt.

* * * * *